US005454274A

United States Patent [19]
Zhu

[11] Patent Number: 5,454,274
[45] Date of Patent: Oct. 3, 1995

[54] SEQUENTIAL COMBINATION LOW TEMPERATURE CONDENSER AND ENCLOSED FILTER SOLVENT REMOVAL SYSTEM, AND METHOD OF USE

[75] Inventor: Jianzhong Zhu, Omaha, Nebr.

[73] Assignee: Cetac Technologies Inc., Omaha, Nebr.

[21] Appl. No.: 247,872

[22] Filed: May 23, 1994

Related U.S. Application Data

[63] Continuation-in-part of Ser. No. 25,665, Mar. 3, 1993, Pat. No. 5,400,665, which is a continuation-in-part of Ser. No. 766,049, Sep. 25, 1991, Pat. No. 5,259,254, and a continuation-in-part of Ser. No. 813,766, Dec. 27, 1991, Pat. No. 5,212,365, and a continuation-in-part of Ser. No. 980,467, Nov. 23, 1992, Pat. No. 5,272,308.

[51] Int. Cl.$^6$ .......... G01N 1/28

[52] U.S. Cl. .......... 73/863.12; 73/864.85; 250/288

[58] Field of Search .......... 73/863.11, 863.12, 73/863.23–863.25, 864.81, 864.85, 864.82, 864.83, 864.84, 864.86, 864.87; 261/78.2; 250/288 R, 288 A; 356/316

[56] References Cited

U.S. PATENT DOCUMENTS

| | | | |
|---|---|---|---|
| 3,735,558 | 5/1973 | Sharstrom et al. | 55/16 |
| 4,109,863 | 8/1978 | Olson et al. | 239/102.2 |
| 4,575,609 | 3/1986 | Fassel et al. | 219/121.59 |
| 4,662,899 | 5/1987 | Tandon | 95/18 |
| 4,730,111 | 3/1988 | Vestal et al. | 250/288 |
| 4,883,958 | 11/1989 | Vestal | 250/288 |
| 4,958,529 | 9/1990 | Vestal et al. | 73/864.81 |
| 4,968,885 | 11/1990 | Willoughby | 73/863.11 X |
| 4,980,057 | 12/1990 | Dorn et al. | 219/198.2 |
| 4,990,740 | 2/1991 | Meyer | 219/121.52 |
| 5,033,541 | 7/1991 | D'Silva | 165/155 |
| 5,145,113 | 9/1992 | Burwell et al. | 239/102.2 |
| 5,192,865 | 3/1993 | Zhu | 250/288 |
| 5,212,365 | 5/1993 | Wiederin | 219/121.52 |
| 5,259,254 | 11/1993 | Zhu et al. | 73/864.81 |
| 5,272,308 | 12/1993 | Wiederin | 219/121.52 |
| 5,400,665 | 3/1995 | Zhu et al. | 73/863.12 |

OTHER PUBLICATIONS

Continuous Filtering, Coalescing & Drying of Process Gases, Kertzman, Perma Pure Products, Inc. pp. 1–8 Sep. 1991.
Perma Pure Mini Dryers Bulletin 106 4 pages by Sep. 1991.

*Primary Examiner*—Thomas P. Noland
*Attorney, Agent, or Firm*—James D. Welch

[57] ABSTRACT

A sequential combination solvent removal system comprising at least one low temperature condenser solvent removal system interconnected to at least one enclosed filter solvent removal system is described. The sequential combination solvent removal system is capable of providing stable levels of solvent vapor in exiting mixtures of solvent vapor and nebulized sample particles, whether the solvent is aqueous or organic, and regardless of the type of sample solution nebulizer used to provide nebulized sample solution droplets to a preceding desolvation system, or of the flow rate of solvent vapor into said sequential combination solvent removal system. In the preferred embodiment a low temperature condenser solvent removal system is first in line and is followed by a functionally attached enclosed filter solvent removal system. A plurality or multiplicity of low temperature condenser and enclosed filter solvent removal systems can be present in modified embodiments in any order, and with or without intervening desolvation systems.

20 Claims, 3 Drawing Sheets

SEQUENTIAL COMBINATION LOW TEMPERATURE CONDENSER AND ENCLOSED FILTER SOLVENT REMOVAL SYSTEM, AND METHOD OF USE

This Application is a Continuation-In-Part of patent application Ser. No. 08/025,665, filed Mar. 23, 1993 and now U.S. Pat. No. 5,400,665, which is assigned to CETAC Technologies Incorporated and which itself was a continuation-in-part of U.S.A. application: Ser. No. 07/766,049 filed Sep. 25, 1991, now U.S. Pat. No. 5,259,254; Ser. No. 07/813,766, filed Dec. 27, 1991, now U.S. Pat. No. 5,212,365; and Ser. No. 07/980,467, filed Nov. 23, 1992, now U.S. Pat. No. 5,272,308.

TECHNICAL FIELD

The present invention relates to a system and method of use for introducing liquid samples into gas-phase or particle detectors, such as inductively coupled plasma atomic emission spectrometers and mass spectrometers. More particularly, the present invention is directed to a system, and method of its use, comprising sequential combination low temperature condenser and enclosed filter solvent removal systems, for use in conjunction with any (e.g. ultrasonic, total consumption direct injection micro nebulizer and other sample solution nebulizer systems), to form a sample introduction solvent removal system which provides efficient solvent removal and long term system operational stability, particularly when a sample is present in an aqueous solvent.

BACKGROUND

The analysis of liquid samples by sample analysis systems which utilize gas-phase or particle detectors, such as inductively coupled plasma (ICP) atomic emission spectrometers, and mass spectrometers is well known. Typically, such sample analysis systems require that a sample solution first be nebulized into sample solution droplets. The sample solution droplets are then typically desolvated, (with the resulting separated solvent being removed by a solvent removal system), to form nebulized sample particles. Said nebulized sample particles are then transported to, and injected into, a detector element of the sample analysis system, wherein they are analyzed. In ICP and other plasma based sample analysis systems for example, the nebulized sample particles are injected into a high temperature plasma where they interact with energy present therein to form fragments such as molecules, atoms and/or ions. Electrons in the molecules, atoms and/or ions are excited to higher energy state orbitals by said interaction. When the electrons relax back into their lower energy, more stable state, orbitals, electromagnetic radiation is emitted. The frequency of the emitted electromagnetic radiation is a "fingerprint" of the contents of the sample and the intensity of the emitted electromagnetic radiation is related to the concentration of the components in the sample.

NEBULIZERS

There are numerous existing systems for producing nebulized sample solution droplets, (which are typically desolvated to form nebulized sample particles), for introduction into gas-phase or particle sample analysis systems. These include pneumatic spray, thermospray, high pressure jet-impact, glass or metal frit, total consumption direct injection micro and ultrasonic nebulizer etc. systems.

For decades pneumatic spray nebulizer systems were the most commonly used sample solution nebulizer systems for introduction of liquid samples into flame and plasma atomic spectrometry, (e.g. atomic emission, atomic absorbtion and atomic fluorescence) as well as mass spectrometers. Pneumatic nebulizers operate by introducing a sample solution through a small orifice into a concentrically flowing gas stream. Interaction between the sample solution and the concentrically flowing gas stream causes production of nebulized sample solution droplets. Pneumatic spray nebulizers, however, produce a wide spectrum of sample solution droplets, as regards the diameter thereof, and limited aerosol sample solution droplet per volume density. This is because relatively large diameter sample solution droplets typically leave the pneumatic nebulizer system under the influence of gravity. Sample analysis systems generally, it will be appreciated, operate with greater sensitivity and provide results which are more reproducable when large numbers of nebulized sample solution droplets are presented for analysis therein, which nebulized sample solution droplets are of a relatively constant and small, (e.g. 13 microns or less) diameter. This is because smaller droplets provide smaller desolvated sample particles which are more easily fragmented to produce molecules, atoms and/or ions. It is noted that the diameters of sample solution droplets formed by a pneumatic nebulization process are dependent on the concentrically flowing gas flow rate and on the size of the small orifice.

A more recently developed approach to nebulizing sample solutions involves use of thermospray nebulizers. Thermospray nebulizers control the temperature of the tip of a capillary tube such that solvent in a sample solution presented thereto, through said capillary tube, is caused to vaporize. The result of said solvent vaporization is formation of nebulized sample solution droplets. Thermospray nebulizers are typically used with mass spectrometer analysis systems as they operate best in low pressures, such as those present at the inlet stages of mass spectrometers. U.S. Pat. Nos. 4,883,958 and 4,958,529 and 4,730,111 to Vestal describe such nebulizing systems. It is noted that the diameters of sample solution droplets formed by the thermospray process are dependent upon the temperature of the capillary tube. It is also noted that the use of elevated temperatures can degrade sample analytes.

A Patent to Willoughby, U.S. Pat. No. 4,968,885 teaches a nebulizing system which uses both thermospray and pneumatic means. Sample solution droplet produced by the process of this nebulizing system have diameters which depend on both temperature and a gas flow rate.

A jet-impact nebulizing system is described by Doherty et al., (Appl. Spec. 38, 405–412, 1984). Said sample solution nebulizing system operates by forcing a sample solution through a nozzle which has an orifice therein on the order of twenty-five (25) to sixty (60) microns in diameter. The ejected sample solution impacts a wall and the interaction therewith causes formation of sample solution droplets. Again, sample solution droplet diameters depend on a flow rate as well as a driving pressure.

A glass frit nebulizer system is described by Layman, (Anal. Chem. 54, 638, 1982). A porous glass frit with numerous pores of a diameter from four (4) to eight (8) microns therethrough is positioned in the flow path of a sample solution. Sample solution which emerges therefrom is highly nebulized but the flow rate of the sample solution is typically low, (e.g. five (5) to fifty (50) microliters/min). While providing well nebulized sample solution droplets, this nebulizer system is prone to inconsistent sample solution flow rates, and must be subjected to repeated wash cycles between applications. It is noted that sample solution droplet diameters are dependent on a driving sample solution pressure.

The above presentation shows that the nebulizing systems surveyed present with various operational limitations. For instance, sample solution droplets produced by pneumatic, jet-impact and thermospray nebulizer systems, or combinations of thereof, have diameters which are dependent on gas flow rates or potentially sample degrading high temperatures. In addition, the glass frit nebulizers have inherent limitations as regards the amount of sample which they can nebulize and depend on a sample solution driving pressure to control sample solution droplet diameters. Said limited sample handling capability in these systems leads to a limit on the sensitivity of sample analysis systems which utilize them. A sample solution nebulizer system which would produce sample solution droplets with diameters determined by some independent variable other than a potentially sample analyte degrading elevated temperature, and which allows efficient sample volume flow handling capabilities would therefore be of utility. The identified attributes are associated with ultrasonic nebulizer systems, and with direct injection micro nebulizer systems.

Briefly, ultrasonic nebulizer systems generally provide means to impinge a sample solution onto, or in close proximity to a vibrating piezoelectric crystal or equivalent which is a part of an oscillator circuit. Typically the oscillator circuit system is calibrated so that radio frequency vibrations are produced. Interaction between the vibrational energy produced by the vibrating piezoelectric crystal or equivalent and the impinging sample solution causes the later to become nebulized into sample solution droplets as a result of the instability of the liquid-gas interface when exposed to a perpendicular force.

It is important to understand that the sample solution droplets produced by ultrasonic nebulizers have diameters which depend on the frequency of vibration of the piezoelectric crystal or equivalent, and that when the frequency of vibration is set to a megahertz level, a theoretically large number (e.g. seventy (70%) percent) of sample solution droplets can be formed with a relatively small uniform diameter of thirteen (13) microns or less. The important limitations of the sample solution nebulizer systems disclosed above are not present, (e.g. sample solution droplet diameters are not dependent on potentially sample analyte degrading elevated temperatures or any flow rates or pressures). Ultrasonic sample solution nebulizing systems are also capable of handling relatively high sample flows, and the sample solution droplet diameters produced by ultrasonic nebulizer system also tend to be more consistent than the diameters of sample solution droplets produced by other nebulizing systems. In addition, the conversion rate of sample solution to nebulized sample solution droplets is theoretically relatively high, being higher than ten (10%) to fifty (50%) percent as compared to approximately two (2%) percent when pneumatic nebulizer systems are used.

The presence of a far larger number and proportion of sample solution droplets with relatively small diameters means two things. First, less sample analyte is lost as a result of relatively large droplets falling away from entry to a detector element in a sample analysis system under the influence of gravity, hence, more sample analyte will be presented to said detector element; and second, the presence of smaller diameter sample solution droplets leads to production of smaller desolvated sample particles which are easier to fragment into molecules, atoms and/or ions for analysis. A larger amount of sample analyte is thus produced per fragmented sample particle. As a result, the sensitivity of a sample analysis system is improved when ultrasonic sample solution nebulizers are used, rather than other sample solution nebulizer systems.

A Patent to Olsen et al., U.S. Pat. No. 4,109,863 describes an ultrasonic nebulizer system in which a piezoelectric crystal or equivalent, (termed a transducer in Olsen et al.) is secured to the inner surface of a glass plate, which glass plate forms a leading portion of an enclosed hollow body, which hollow body is positioned in an aerosol chamber. The purpose of the glass plate is to provide the transducer protection against corrosion etc. which can result from contact with components in sample solutions. The glass plate is typically one-half (0.5) wavelengths of the transducer vibrational wavelength utilized, thick. This thickness optimizes effective transfer of vibrational energy therethrough. During use a sample solution is impinged upon the outer aspect of the glass plate, inside the aerosol chamber, rather than onto the transducer per se. The transducer is caused to vibrate and the interaction between the impinging sample solution and the vibrational energy produced causes production of nebulized sample solution droplets. In addition, a liquid coolant is circulated within the hollow body to maintain the transducer at a desired temperature. Problems which users of the Olsen et al. invention have experienced result from the use of a liquid to cool the transducer, and the use of a carrier gas injected from below the location of the transducer in the aerosol chamber. (It is noted that said carrier gas serves to sweep nebulized sample solution droplets toward a detector element in an analysis system). Even though the piezoelectric crystal is oriented vertically, bubbles tend to form on the back side of the transducer during use, resulting in uneven cooling of the transducer. This leads to reduced operational efficiency and lifetime of the transducer. In addition, the electrical leads to the transducer, from the other components of an oscillator circuit, pass through the cooling liquid, and they tend to become corroded during use. Continuing, injecting a carrier gas into the aerosol chamber from a position below the location of the piezoelectric crystal or equivalent, as is done in the Olsen et al. ultrasonic nebulizer system, leads to pulsations in the volume density of the aerosol sample solution droplets which are produced over time which are available to sample analysis systems. In addition, the hollow body of the Olsen et al. invention is attached to the aerosol chamber thereof in a manner which creates "crevasses" therebetween. Sample from one analysis procedure can accumulate in the crevasses and by a "carry-over" capillary action or "wicking" effect be released and contaminate analysis results in subsequent analysis procedures. Continuing, the Olsen et al. invention directs nebulized sample solution droplet flow toward solvent vaporization, desolvation and sample analysis system detector elements by way of a relatively small diameter orifice. Turbulence results when the nebulized sample solution droplets pass through said relatively small diameter orifice and nebulized sample solution droplets are caused to reagglomerate, and are lost, as a result thereof. Finally, the hollow body construction of the Olsen et al. invention does not provide any vibrational energy focusing capability, since the vibrational energy produced by the transducer is emitted in all directions therefrom, without any means being present to redirect any of said vibrational energy.

A Patent to Dorn et al. U.S. Pat. No. 4,980,057 describes a sample solution nebulizer system which uses both ultrasonic and pneumatic means to nebulize sample solutions. A one-sixteenth (1/16) inch stainless steel tube is placed in the center of an ultrasonic nebulizer probe and serves to concentrate the vibrational energy produced by an ultrasonic transducer present therearound. A fused silica capillary tube is placed inside the one-sixteenth (1/16) inch stainless steel tube to, during use, deliver a high velocity gas stream to the tip of the ultrasonic nebulizer probe. Also during use, the sample solution is introduced to the surface of the ultrasonic nebulizer probe. Interaction between the sample solution, vibrational energy and high velocity gas stream causes the sample solution to be nebulized into sample solution droplets. It is noted that this system probably can not utilize megahertz level frequencies as the ultrasonic nebulizer probe is not of a small enough dimension, (e.g. on the order of half a wavelength of a megahertz vibrational frequency), to efficiently transmit megahertz wavelength vibrational energy waves to the location at which the sample solution is entered to the system. The Dorn et al. Patent teaches the use of one-hundred-and-twenty (120 KHZ) Kilohertz operational frequency. In addition, this system produces sample solution droplets, the diameters of which are affected by the flow rate of the sample solution nebulizing gas, as is the case with any pneumatic type sample solution nebulizing system.

A paper by Goulden et al., (Anal. Chem 56, 2327–2329, 1984) describes a modified ultrasonic nebulizer. The piezoelectric crystal or equivalent, termed a transducer in the Goulden paper, is oriented horizontally at the upper aspect of a glass container. A rubber stopper is placed below the transducer, inside the walls of the glass container. The rubber stopper has a vertically oriented centrally located hole therethrough such that a large amount of cooling water, (e.g. one-half (0.5) l/min) can be caused to flow vertically upward through said vertically oriented centrally located hole in the rubber stopper, into the space between the lower surface of the transducer and the upper surface of the rubber stopper, and out thereof around the edges of the rubber stopper and inside the glass container. The purpose of the described arrangement is to prevent bubbles from accumulating under the transducer during use, and thereby avoid instabilities of operation and reduced transducer lifetime.

A paper by Karnicky et al., (Anal. Chem., 59, 327–333, 1987) describes another design for an ultrasonic nebulizer. An enclosed chamber has, at a distance above the inside surface at of its lower extent, a piezoelectric crystal or equivalent, termed an ultrasonic transducer in the Karnicky paper, which ultrasonic transducer fits snuggly within the inner side walls of the enclosed chamber. Air is present between the upper surface of the lower extent of the enclosed chamber, and the lower surface of the ultrasonic transducer, but between the upper surface of the ultrasonic transducer and the lower surface of a glass diaphragm which is present at the upper aspect of the enclosed chamber, there exists a space through which cooling water is flowed during use. The ultrasonic transducer is shaped concave upward so that vibrational energy produced thereby during use is directed to and focused upon the glass diaphragm through the cooling water. An enclosed sample solution entry and carrier gas entry assembly mounts to the enclosed chamber above the location of the glass diaphram. During use the enclosed chamber with ultrasonic transducer therein, and with the enclosed sample solution and carrier gas entry assembly mounted thereto is oriented with its longitudinal axis at an approximate fourty-five degree angle to an underlying horizontal surface. A sample solution is entered so that it impinges on the outer surface of the glass diaphragm at an approximate fourty-five degree angle thereto. Interaction between vibrational energy produced by the ultrasonic transducer and the impinging sample solution produces nebulized sample solution droplets which are then transported to desolvation and solvent removal systems under the influence of a pressure gradient created by the entering of a carrier gas flow to the enclosed sample solution and carrier gas entry assembly. It is also noted that the Karnicky system provides a wick which contacts the outer surface of the glass diaphragm to drain away sample solution which is not nebulized during use.

Another paper, by Mermet et al., (Der. Atomic Plasma Spec. Anal. Proc. Winter Conference, 245–250, 1980), describes yet another design for an ultrasonic nebulizer system. A piezoelectric crystal or equivalent, termed a transducer in the Mermet paper, is present within a waveguide structure which decreases in inner diameter along its upwardly projecting longitudinal axis, near the lower extent thereof. The internal waveguide structure is thus, conical in shape, and during use is filled with a vibrational energy transmitting bath. Said waveguide structure shape plays the role of an impedance transformer and use of low electrical power levels, (e.g. five (5) to seven (7) watts) to effect sample solution nebulization is made possibly, thereby reducing transducer cooling requirements. At the upper extent of said waveguide structure is present a nebulization cell, the lower extent of which is made from a thin membrane of ethylene polyterephtalate (Mylar, Terphane) which is transparent to ultrasonic energy vibrational energy. During use a sample solution is entered to the nebulization cell and vibrational energy produced by the transducer is directed by the waveguide structure through the vibrational energy transmitting bath into the nebulization cell where it interacts with the entered sample solution to form sample solution droplets. Said nebulized sample solution droplets are then transported to additional sample preparation stages under the influence of a pressure gradient created by entering a carrier gas flow to the nebulization chamber.

A recent Patent to Burwell et al., U.S. Pat. No. 5,145,113 describes a system which utilizes ultrasonic nebulization as a means to provide droplets with an array of diameters. By causing said droplets to maneuver around a separator plate, under the influence of a carrier gas flow, relatively large diameter droplets are eliminated while relatively small diameter droplets are transported through a nozzle outlet. The Burwell invention primary focus then, is upon selecting nebulized droplets produced by ultrasonic nebulization, which nebulized droplets have a relatively small diameter.

The above summary of relevant references shows that while ultrasonic nebulizer systems provide benefits as compared to other nebulization systems, problems still exist. Problems with operational stability and piezoelectric crystal or equivalent lifetime develop as a result of uneven cooling thereof during use, when bubbles form in a cooling liquid where it meets the piezoelectric crystal or equivalent. In addition, ultrasonic energy produced by a vibrating piezoelectric crystal or equivalent in most ultrasonic nebulizer systems is not well directed for use in nebulizing a sample solution, to a point at which a sample solution is present. Other problems result from injecting a carrier gas meant to carry nebulized sample solution droplets toward a detector in a sample analysis system, at nonoptimum locations and in nonoptimum directions. This leads to formation of turbulence in nebulized sample solution droplet flows and accompanying reagglomeration of nebulized sample solution droplets. This effect is worsened by the presence of relatively small orifices in the flow paths of nebulized sample solution droplets present in the aerosol chambers of some inventions. Also, the presence of crevasses in the aerosol chamber of some inventions leads to sample carry-over from one analysis procedure to a subsequent analysis procedure. Additional complications result, in some inventions, from the use of pneumatic nebulization means in addition to ultrasonic means, and from the use of system geometry which limits the ultrasonic nebulizer operational frequency to less than megahertz levels.

An ultrasonic nebulizer system which serves to overcome many of the problems identified above is taught in a Patent to Zhu et al., U.S. Pat. No. 5,259,254, (assigned to CETAC TECHNOLOGIES INC.). The system of the Zhu et al. ultrasonic nebulizer is disclosed in the Detailed Description Section of this Disclosure as an example of a sample solution nebulizer system used in the sequential combination solvent removal system of the present invention. As a result said invention is not further discussed here.

Continuing, it should also be understood that sample solution nebulization is typically carried out in an aerosol chamber at a location remote from a sample analysis system, (as described above with respect to pneumatic and ultrasonic nebulizer systems etc.), and nebulized sample droplets must be transported to the location of the sample analysis system by way of a connection means. A common problem which occurs during use is that nebulized sample is lost by adherence to the internal walls of the aerosol chamber and connection means between the output of the sample nebulizer system and the input to the sample analysis system. Additionally, the aerosol chamber and connecting means volume must be filled with nebulized sample to cause nebulized sample to eject from said connection means into the remotely located sample analysis system. A relatively larger amount of nebulized sample must then be prepared than would be the case if the sample nebulizer system had no aerosol chamber and was situated in closer proximity to the sample analysis system. System sensitivity is, as a result, adversely affected and tedious, time consuming, system flushing procedures are often required to prevent sample carry-over from one analysis procedure from contaminating subsequent analysis procedure results. It would then, be very beneficial if a sample nebulizer system which did not require an aerosol chamber and which could be positioned closely adjacent to sample analysis systems were available.

An approach to nebulizing sample which can overcome the identified problem utilizes total consumption direct injection micro nebulizing systems such as described in U.S. Pat. No. 4,575,609 to Fassel et al., and by Baldwin and McLafferty, (Org. Mass Spect. 7, 1353, 1973), and by Wiederin et al. (Anal. Chem. 63, 219, 1991). A recent Patent to Meyer, U.S. Pat. No. 4,990,740 describes an intraspray torch which serves to overcome some of the problems associated with usage of the Fassel invention. U.S. Pat. Nos. 5,272,308 and 5,212,365 to Wiederin, discussed briefly supra, (both are assigned to CETAC TECHNOLOGIES INC.), teach improved direct injection micro nebulizers. Direct injection micro nebulizer systems have the important advantage of being able to provide essentially all of the analyte in a sample solution entered thereto, to the detector element in a closely situated sample analysis system. Sample carry-over from one analysis procedure to a subsequent analysis procedure is also minimized by the relatively very small internal volume thereof. Very low flow rate capacity, (e.g. one (1) to one-hundred (100) microliters/min), however, limits the total amount of analyte in a sample solution entered thereto which can reach a detection element in an analysis system. As a result analysis system sensitivity is not greatly improved by their use. It is noted that sample solution droplet diameters depend on a pressure driven sample solution flow rate.

The Fassel et al. Patent teachings are that the micro nebulizer should be inserted directly into a standard torch of the type used in Inductively Coupled Plasma sample analysis procedures, in which standard torch, during use, a plasma is formed. The micro nebulizer is designed to perform sample solution nebulization directly. That is, the aerosol chamber internal volume and connection means internal volume, between the sample nebulizer system and a remotely located sample analysis system, are eliminated.

The Fassel et al. invention assumes the presence of a first tube, which first tube is essentially the sample injector tube of a inductively coupled plasma standard torch. Briefly, to aid with understanding, said standard torch is comprised of a series of elongated concentric tubes, which concentric tubes are typically, but not necessarily, made of quartz. The centermost tube is typically termed the sample injector tube. It is typically circumscribed by an intermediate tube, which intermediate tube is typically circumscribed by an outer tube. One can visualize the torch system in side elevation, from a position perpendicularly removed therefrom, with the longitudinal dimensions of the various elongated tubes projecting vertically upward from an underlying horizontal surface. Sample particles from a typical sample nebulizing system are typically injected vertically into the sample injector tube of the standard torch from a sample access port at the vertically lower aspect thereof, and caused to flow through said sample injector tube to the upper aspect thereof under the influence of a pressure gradient, whereat they are ejected into the space above said upper aspect of the sample injector tube, which space is typically within the volume circumscribed by the outer tube of the standard torch system, in which space a plasma is typically created during use. As well, typically tangentially injected gas flows are entered into the annular spaces between the outer surface of the sample injector tube and the inner surface of the intermediate tube, and between the outer surface of the intermediate tube and the inner surface of the outer tube. (Note, tangential is to be understood to mean that a gas flow follows a spiral-like upward locus path from its point of entry to the standard torch). The typically tangentially injected gas flows are entered by way of intermediate and outer ports also present in the torch. Said typically tangentially injected gas flows serve to shield the various tubes which they contact from the intense temperatures and heat formed by creation of a plasma in the upper aspects of the torch, and to some extent aid sample flow into the plasma associated area.

The Fassel et al. invention teaches that rather than enter a previously, distally, nebulized sample to the sample access port of a standard torch, a micro nebulizer should be entered into the sample injector tube and positioned so that the upper aspect thereof is at an essentially equal vertical level with the upper aspect of the sample injector tube of the standard torch, into which the micro nebulizer is inserted. Sample solution is then entered into the micro nebulizer via a sample delivery inner tube, directly, without any prior sample nebulization being performed thereon. The Fassel et al. micro nebulizer is designed to cause sample solution entered thereto, to eject from the upper aspect of the micro nebulizer and thereby become nebulized. The upper aspect of the sample delivery inner tube thereof, is positioned at essentially the same vertical level as the upper aspect of the sample injector tube of the standard torch, hence, is located very near the position at which a plasma can be created for use in analysis of the ejected nebulized sample. It will be appreciated that the only nebulizer internal volume which exists is that within the micro nebulizer and the associated connection means thereto from the source of sample solution. Said internal volume is typically on the order of five (5) microliters and is orders of magnitude smaller than the internal volume associated with the sample injector tube of a standard torch and the connecting means thereto from a remotely located conventional sample solution nebulizer system.

To better understand the Fassel et al. micro nebulizer it is necessary to better describe the system thereof. Basically, the Fassel et al. micro nebulizer is comprised of an inner tube and an outer tube, which inner tube is concentrically circumscribed by said outer tube. The two concentric tubes are oriented vertically and placed into the first tube, which first tube can be thought of as the sample injector tube of a standard torch as described above. A sample solution of can be entered into the micro nebulizer at the lower aspect of the inner tube thereof and caused, under the influence of a pressure gradient, (typically 100 to 1000 psi), to flow vertically upward and eject from the upper aspect of the inner tube of the micro nebulizer. Sample solution velocities on the order of one-hundred (100) meters-per-second are common. In addition, a gas flow can be entered into the annular space between the outer surface of the inner tube and the inner surface of the outer tube of the micro nebulizer, which gas flow interacts with the sample solution flow at the point of its ejection from the inner tube of the micro nebulizer, thereby causing said sample solution to be nebulized by essentially pneumatic means. An additional gas flow can be injected into the annular space which results between the outer surface of the outer tube of the micro nebulizer and the inner surface of the sample injector tube of the standard torch into which the Fassel et al. micro nebulizer is inserted. Said additional gas flow can also aid with the sample solution nebulization effect. The nebulized sample solution then immediately injects into the space in the standard torch in which a plasma can be created. The disclosure of the Fassel et al. Patent teaches that a support tube should be epoxied to the outer surface of the outer tube of the micro nebulizer, along some portion thereof which is inside the first tube, (ie. sample injector tube of the standard torch), during use, apparently to protect the outer and inner tubes thereof against being crushed when inserted into the sample injector tube of the standard torch, and to aid with a firm fit within the sample injector tube of the standard torch into which the micro nebulizer is inserted. The Fassel et al. disclosure teachings also indicate that the outer and inner tubes of the micro nebulizer should be attached to the standard torch by way of a fixed fitting, and that the upper aspect of the inner tube of the micro nebulizer should be positioned vertically at a level below the upper aspect of the sample injector tube of the standard torch. The drawings of Fassel et al. show that the upper aspect of said inner tube of the micro nebulizer is also placed vertically below the upper aspect of the outer tube of the micro nebulizer and that said outer tube of the micro nebulizer and the sample injector tube of the standard torch are tapered inwardly at their upper aspects. In use, it has been found, that the Fassel et al. system as described above, particularly when used with high solids content sample solutions, becomes clogged at the upper aspect thereof. This results in the necessity that the micro nebulizer be cleaned often, which cleaning is difficult to perform and often leads to breakage of the micro nebulizer. It has also been discovered that the upper aspect of the inner tube of the Fassel et al. system is difficult to position inside the outer tube of the Fassel et al. system, and that the Fassel et al. system tends dislodge from the point at which it is secured inside the standard torch sample injector tube at the lower aspect of said sample injector tube, when relatively high pressure gas flow is entered into the annular space between the outer surface of the outer tube of the micro nebulizer and the inner surface of the sample injector tube of the standard torch. It is emphasized that the securing of the micro nebulizer to the inside of the sample injector tube of the standard torch is by way of a fitting, through which fitting is run the outer and inner tubes of the micro nebulizer.

Another Patent, U.S. Pat. No. 4,990,740 to Meyer, recognizes the benefits and problems associated with the Fassel et al. micronebulizer, and teaches an Intraspray ICP Torch which serves to overcome some of said problems. The Meyer invention, in essence, provides a low operational pressure equivalent to a micronebulizer system at the lower aspect thereof, and also provides a series of impactors thereabove in a torch system portion of the invention. The Meyer invention provides greater stability in both construction and in nebulized sample solution flow to an ICP. Said impactors serve to deflect large diameter droplets (e.g. over approximately fifteen (15) microns in diameter), and prevent their ejection from the upper aspect of the invention, and in addition to buffer the ejected flow of nebulized sample solution.

In view of the benefits provided by the Fassel et al. micro nebulizer, and in view of the difficulties associated with use thereof, which difficulties have received recognition from users thereof, there was demonstrated a need for an improved direct injection micro nebulizer system. Patents to Wiederin, U.S. Pat. Nos. 5,212,365 and 5,272,308, (assigned to CETAC TECHNOLOGIES INC.), teach such an improved direct injection micro nebulizer system. Briefly, said improved direct injection micro nebulizer system is comprised of an elongated primary body element with a removable top element at the top thereof and with a sample delivery tube system adjustment means attached to the bottom thereof. In use said direct injection micro nebulizer system can be entered to the inner space of a sample injection tube of a standard torch used with inductively coupled plasma sample analysis systems, or into the inner space of a tube in a specially designed torch which has no sample injector tube per se., for instance. As well, because the Wiederin invention does not require the presence of a sample injector tube for its structural integrity, as does the Fassel et al. system), it can be utilized in systems in which no torch is present. That is, the Wiederin system can be easily used with other than plasma based sample analysis systems, such as for instance, mass spectrometers. Continuing, the primary body element then of the Welderin direct injection micro nebulizer, then allows for connections at the lower, and upper vertically oriented aspects thereof, and also allows for a connection at a midpoint of the primary body element. The connection at the upper aspect thereof being, as mentioned, to allow removal of a top element. This allows easy access and cleaning of accumulated sample solids which accumulate inside the primary body element during use and eases the task of threading a sample delivery tube through a hole in said top element when constructing the system. The connection at the lower aspect thereof being, as mentioned, to accommodate attachment of a sample delivery tube adjustment means which allows the upper aspect of the sample delivery tube to be easily positioning with respect to the primary body element, without applying potentially damaging stresses to the system. The connection at the middle of said primary body element, in contrast to the connections at the upper and lower ends of the primary body element, is present to allow attachment to a source of gas to allow causing a flow thereof into the annular space between the outer surface of the sample delivery tube of the Wiederin direct injection micronebulizer and the inner surface of primary body element thereof during use. It is the interaction at the top aspect of the system, between said gas flow entered at the middle connection which exits at the top aspect of the system, and sample which is entered to the system by the sample delivery tube which exits said sample delivery tube at the upper aspect of said system, which leads to sample nebulization in an analogically equivalent manner to that which occurs in the Fassel et al. system during use.

The Wiederin system then allows easy access the to inner portion of the upper aspect of the micro nebulizer, and easy insertion and adjustment of the vertical location of the upper aspect of the sample delivery thereof, and use in both plasma based and other than plasma based sample analysis system.

Other improvements provided by the Wiederin system include the use of a protective sleeve around at least a portion of the extent of the sample delivery tube to prevent its becoming crushed in use, use of hydrofluoric acid resistant nonmetalic materials in the construction thereof. The use of only nonmetalic materials prevents untoward interaction with plasma energy which is common when metals are present near a plasma, and the use of hydrofluoric resistant materials, (e.g. polyimides), allows use of hydrofluoric acid as a sample solvent.

The above summary of sample solution nebulizers serves to demonstrate that many systems which serve to nebulize sample solution exist. The present invention, it is emphasized, can be utilized with any sample solution nebulizer system.

SOLVENT REMOVAL SYSTEMS

Continuing, as mentioned at the outset, sample solution preparation for introduction to a detector element in a sample analysis system typically involves not only a sample solution nebulization step, but also sample desolvation and solvent removal steps. Solvent is typically removed from nebulized sample solution droplets prior to being entered to, for instance, an ICP based sample analysis system. If this is not done, and done rather well, plasma instability and spectra emission interference can occur in plasma based analysis systems, and as well, solvent outgassing in MS systems can cause pressures therein to rise to unacceptable levels.

Conversion of sample solution droplets to nebulized sample particles involves two processes. First, sample solution droplets are desolvated by a heating process to vaporize solvent present and provide a mixture of solvent vapor and nebulized sample particles; and second, the solvent vapor is removed.

The most common approach to removing solvent is exclusively by use of a low temperature condenser system. Briefly, in use said low temperature condenser system accept a mixture of nebulized sample particles and vaporized solvent provided by a desolvation system, and serves to condense and remove the solvent vapor. When the solvent present is water very high desolvation efficiency, (e.g. ninty-nine (99%) percent), is typically achieved, when the solvent condensing temperature is set to zero (0) to minus-five (–5) degrees centigrade. However, when organic solvents are present the desolvation efficiency at the indicated temperatures is typically reduced to less than fifty (50%) percent. Use of lower temperatures, (e.g. minus-seventy (–70) degrees centigrade), can improve the solvent removal efficiency, but greater loss of nebulized sample particles by condensing solvent vapor is typically an undesirable accompanying effect. In addition, low temperature desolvation systems typically comprise a relatively large volume condenser. This can lead to sample "carry-over" problems from one analysis procedure to a subsequent analysis procedure as it is difficult to fully flush out the relatively large volume between analysis procedures.

A Patent to D'Silva, U.S. Pat. No. 5,033,541, (assigned to CETAC TECHNOLOGIES INC.), describes a high efficiency double pass tandem cooling aerosol condenser desolvation system which has been successfully used to desolvate ultrasonically nebulized sample droplets. This invention presents a relatively small internal condenser volume, hence minimizes sample carry-over problems, however, while the invention operates at high desolvation efficiencies when water is the solvent involved, it still operates at lower desolvation efficiencies when organic solvents are used. The invention also requires sample passing therethrough to undergo turbulance creating direction reversals, and the use of relatively expensive refrigeration equipments. Turbulence in a nebulized sample flow path can cause reagglomeration of nebulized sample solution droplets and, especially when very low temperatures are present, recapture of nebulized desolvated sample particles present.

Another approach to removing solvent vapor involves the use of enclosed filter systems. Systems using said approach provide a filter formed to provide an enclosed volume through which a mixture of solvent vapor and nebulized particles is caused to flow. Said Solvent vapor is able to diffuse through said filter material, but said nebulized particles are too large, and remain within. Said diffusing solvent vapor is typically removed by a flow of gas outside the enclosed filter. Said enclosed filter serves then to guide said nebulized particles toward a sample analysis system while removing solvent vapor.

A Patent to Skarstrom et al., U.S. Pat. No. 3,735,558 describes a counter-flow hollow tube(s) enclosed filter, mixed fluids key component removal system. Briefly, the invention operates to cause separation of key components from mixed fluids, such as water vapor from air, by entering the mixed fluid at one end of a single, or a series of, hollow tube(s), the walls of which are selectively permeable to the key components of the mixed fluid which are to be removed. A gas is entered to the system at the opposite end of the hollow tube(s), which gas is caused to flow over the outside of the hollow tube(s) in a direction counter to that of the mixed fluids, to provide an external purge of the key components of the mixed fluid which diffuse across the hollow tube(s). Diffusion of key components is driven by pressure and concentration gradients across the hollow tube(s). This approach to removal of diffusing components does not require the presence of low temperature producing refrigeration equipments, and presents a relatively small internal volume.

Two Patents to Vestal, U.S. Pat. Nos. 4,958,529 and 4,883,958 also describe systems which utilize counter-flow enclosed filters systems, with the application being to remove solvent vapor from nebulized samples produced by a spraying technique. The Vestal Patents state that the properties of the filter material used are not critical to the operation of the invention, but suggest the use of filter material available under the tradename of ZITEX. Said filter material provides a pore size of from two (2) to five (5) microns with a corresponding porosity of up to sixty (60%) percent. ZITEX is typically available in sheet form and enclosed filters made therefrom are typically constructed from a multiplicity of spacers and two sheets thereof. To provide an enclosed filter which is sufficiently long to provide reliable solvent vapor removal, in a reasonable space, it is typically necessary to arrange the spacers in a pattern which requires many severe sample flow path direction changes. A flow of solvent vapor and nebulized sample particles passing through such a tortuous pathway experiences turbulence. Turbulence causes sample to adhere and accumulate inside the enclosed filter thereby causing sample carry-over problems. The Vestal Patents also describe the heating of the enclosed filter to further assure continuous vaporization of solvent vapor present therein, and the flow of a gas outside the enclosed filter to remove solvent which diffuses through the enclosed filter.

A Patent to Zhu et al., U.S. Pat. No. 5,259,254, (assigned to CETAC TECHNOLOGIES INC.), teaches the use of sequential desolvation and enclosed filter solvent removal systems in conjunction with a very efficient ultrasonic nebulizer system. Another Patent, U.S. Pat. No. 5,272,308 to Wiederin, (assigned to CETAC TECHNOLOGIES INC.), teaches the use of a similar sequential desolvation and enclosed filter solvent removal system with a very convenient and efficient direct injection total consumption micro nebulizer system.

A problem during the use of the enclosed filter solvent removal systems taught in said Zhu et al. and Wiederin Patents, however, has been identified when a relatively large amount of aqueous solvent, for the relative sized of the enclosed filter elements, is presented to the enclosed filter solvent removal system for removal. That is, the problem's occurrence is dependent upon specific enclosed filter system dimensions and solvent vapor flow rates, but it has been noted that when aqueous solvent is utilized, the efficiency of the enclosed filter solvent removal system can become erratic or can cycle with time when solvent vapor flow rates exceed some level. When the volume of solvent vapor provided to the enclosed filter solvent removal system is kept below said level for the specific enclosed filter solvent removal system involved, however, the problem does not appear. Hence, a system including a means preceeding an enclosed filter solvent removal system which would serve to remove a majority of aqueous solvent vapor prior entry to said enclosed filter solvent removal system, would be of utility.

In summary, the above presentation shows that the preparation of liquid samples for analysis in gas phase or particle analysis systems typically involves:

1. Nebulizing a sample solution to form sample solution droplets.
2. Desolvating the resulting nebulized sample solution droplets to provide a mixture of nebulized sample particles and solvent vapor.
3 Removing said solvent vapor to provide desolvated nebulized sample particles.
4. Transporting said desolvated nebulized sample particles through the nebulizing system, desolvation and solvent removal systems into a detector of a sample analysis system.
5. Doing the above with varying degrees of success as regards use with either water or organic solvents, minimizing sample carry-over from one analysis procedure to a subsequent analysis procedure and achieving long term stability of operation.

In view of the above it can be concluded that a solvent removal system for use in nebulized sample particle introduction systems, which can at once: successfully remove solvent vapor introduced thereto at various, (including relatively high for the size thereof), level inflow rates; be used with any sample solution nebulizer system; provide more efficient, (e.g. ninty-nine and nine-tenths, (99.9%) and better percent, desolvation and solvent removal from presented nebulized sample solution droplets in a manner which is equally successful whether water or organic solvents are present; and which optimizes system long term operational stability, particularly when aqueous solvents are present, would be of great utility. Such a sample introduction system is taught by the present invention.

DISCLOSURE OF THE INVENTION

The Background Section of this Disclosure provides a rather extensive summary of systems and methods which serve to nebulize sample solutions, and which serve to desolvate and remove resulting solvent vapor from nebulized sample solution droplets, prior to the injection of resulting nebulized sample particles into a sample analysis system.

The summary of the many systems for use in nebulizing sample solutions was included to make clear that the present invention can be utilized with any known sample solution nebulization system, although the preferred sample solution nebulizing system of the present invention is the U5000AT ultrasonic nebulizer produced by CETAC TECHNOLOGIES INC. of Omaha, Nebr. Said ultrasonic nebulizer is described in the Detailed Description Section of this Disclosure.

The summary of the various solvent removal systems was presented to provide insight to the fact that there are basically two approaches to removing solvent vapor from a mixture with nebulized sample particles which result when nebulized sample solution droplets, provided by a sample solution nebulizing system, are subjected to an elevated temperature. Said approaches being: first, the use of low temperature condenser solvent removal systems, and second, the use of enclosed filter solvent removal systems. The later of which approaches can utilize a flow of solvent vapor removing gas over the outer surface of an enclosed filter per se. to remove solvent vapor which diffuses through said enclosed filter per se., or can utilize a low temperature condenser means outside said enclosed filter per se. which serves to condense said solvent vapor which diffuses through said enclosed filter per se.

As mentioned in the Background Section, low temperature condensers are particularly well suited to the removal of aqueous solvent vapor produced by the application of an elevated temperature to nebulized sample droplets provided by a sample solution nebulizer system. Typically ninety-nine, (99%), of water vapor introduced to a low temperature condenser will be removed thereby when the temperature thereof is held near zero (0.0) degrees centigrade. However, it was also noted in the Background Section that when an organic solvent is present, low temperature condensers remove on the order of only fifty, (50%), percent of solvent vapor present, depending on the temperature utilized. As well, it was noted that enclosed filter solvent removal systems can be equally successful in removing solvent vapor whether the solvent is aqueous or organic.

It is to be appreciated, however, that a problem has been found to exist when enclosed filter solvent removal systems are used "exclusively" to remove aqueous solvent vapor. Said problem being that when the flow of solvent vapor and nebulized sample particles presented thereto by a desolvating system exceeds some level, (which level is determined by the enclosed filter solvent removal system design parameters, such as overall size), the level of water vapor content exiting said enclosed filter solvent removal system with nebulized sample particles, varies with time. Said variance in the level of water vapor content, it is also noted, can be erratic or cyclical and, it is emphasized, can be very detrimental to the stability of, for instance, a plasma into which it is injected.

The cause of the problem is believed to be that while water vapor diffuses through an enclosed filter per se. of an enclosed filter solvent removal system as desired, when the level of solvent vapor outside said enclosed filter per se. is kept low, this does not remain true when that level is less well controlled. In that light it must be appreciated that it is difficult to control the rate of water vapor removal from the space between the outer surface of an enclosed filter per se., and the inner surface of a containing structure by, for instance, a flow of gas over the outer surface of said enclosed filer per se., when the solvent vapor flow rate into said enclosed filter per se. exceeds a critical value, said critical value being specific to an enclosed filter system. It is believed that water vapor also condenses in the space between the outer surface of the enclosed filter and the inner surface of enclosed filter containing structure leading to cyclical plugging of the drain therefrom. This leads to pressure swings inside the identified space during use. It is mentioned that the identified problem has not been found to exist, however, when an organic solvent is used.

For example, the signal from an inductively coupled plasma sample analysis system was monitored. The present invention improved the relative standard deviation, (that is the spread in the data), achieved when a one (1) part per million manganese sample present in an aqueous solution provided to said inductively coupled plasma sample analysis system by the present invention, was detected thereby. In particular, in one experiment, when an enclosed filter solvent removal system alone was present, the relative standard deviation was on the order of six (6) to ten (10). However, when a sequential combination of a low temperature solvent removal system followed by an enclosed filter solvent removal system was utilized in the same experiment, the relative standard deviation in the data was on the order of one (1) to two (2). It should then be appreciated that the present invention provides stability in achievable test results.

The present invention then is primarily a system comprised of a sequential combination of both low temperature condenser and enclosed filter solvent removal systems. Said invention, in its preferred embodiment, provides that a majority of water vapor present in a mixture of nebulized sample particles and solvent water vapor provided by the heating of nebulized sample solution droplets in a desolvation system, be removed by a low temperature condenser solvent removal system prior to entry of remaining nebulized sample particles and water vapor into an enclosed filter solvent removal system. That is, the present invention teaches that enclosed filter solvent removal system(s) should be used in sequential combination with low temperature condenser solvent removal system(s) to provide a surprisingly stable solvent level content output therefrom during prolonged use. It is not then the specific design of either type of solvent removal system that is the focus of the present invention, but rather it is the presence of both types thereof in a sequential combination solvent removal system. It has been found that the described present invention provides exceptionally stable solvent vapor output levels.

It is further noted that while the first solvent removal system in the sequential combination solvent removal system of the present invention is typically a low temperature condenser solvent removal system, which serves to remove a vast majority of aqueous solvent vapor before it can enter an enclosed filter solvent removal system, this need not be the case to be within the scope of the present invention. As well, it is within the scope of the present invention to provide multiple solvent removal systems of one type (ie. low temperature condenser or enclosed filter), in direct attachment to one another as long as at least one of each type of solvent removal system is present.

It is also noted that the present invention can be comprised of any number of sequential low temperature condenser and enclosed filter solvent removal systems, with or without high temperature providing desolvation systems present between each of said sequential solvent removal systems.

The present invention will be better understood by reference to the Detailed Description Section of this Disclosure, in conjunction with the accompanying Drawings.

SUMMARY OF THE INVENTION

The use of sample solution nebulizers to nebulize sample solutions into sample solution droplets, prior to entry thereof into sample analysis systems, is known. Also known is the use of desolvation systems which serve to heat said sample solution droplets to produce a mixture of nebulized sample particles and solvent vapor. Also known are low temperature condenser and enclosed filter solvent removal systems for use in removing said solvent vapor from said mixture of solvent vapor and nebulized sample particles.

Known systems for producing desolvated nebulized sample particles from sample solutions utilize any of a large number of different type nebulizers as described in the Background Section of this Disclosure, (e.g. pneumatic, thermospray, direct injection total consumption micro nebulizers, ultrasonic etc.), but each utilizes only one type of solvent removal system, assuming solvent removal is required. That is, either a low temperature condenser or an enclosed solvent removal system is used with a sample solution nebulizer system. No known system utilizes both low temperature condenser and enclosed filter solvent removal system(s) in sequential combination, emphasis added.

While enclosed filter solvent removal systems are generally capable of removing ninty-nine-and-nine-tenths (99.9%) percent or more of solvent vapor entered thereto, whether said solvent is aqueous or organic, it has been discovered that when enclosed filter solvent removal systems are used exclusively to remove water vapor, the resulting level of water vapor exiting said enclosed filter solvent removal system can be erratic if the flow rate of said water vapor into said enclosed filter becomes to great. That is, the water vapor content of exiting mixture of nebulized sample particles and solvent vapor can be far from constant, and can even vary cyclically with time.

It is generally known that low temperature condenser solvent removal systems are extremely well suited for the removal of water vapor. Typical low temperature condenser systems can consistently remove ninty-nine (99%) percent of all water vapor entered thereto when a temperature of zero (0.0) degrees centigrade is used, although they are less effective when organic solvents are present. At zero (0.0) degrees centigrade a low temperature condenser solvent removal system will remove approximately fifty (50%) of organic solvent present. It is also known that enclosed filter solvent removal systems are equally successful at removing aqueous or organic solvent vapor entered thereto when the flow rate of said water vapor is not too great for the design parameters, such as overall size, of an enclosed filter solvent removal system. It has been discovered, however, that enclosed filter solvent removal systems can provide less than stable exiting water vapor levels when the flow rate of entering water vapor becomes too great. It is emphasized that a varying water vapor level when entered to, for instance, a plasma in a plasma based sample analysis system, can serve to cause instability in said plasma, and even, in the extreme, cause it to be extinguished.

The present invention, in recognition of the identified problem, provides that low temperature condenser and enclosed filter solvent removal systems should be utilized in sequential combination. That is, a mixture containing water vapor and nebulized sample particles should, when desolvation and solvent removal is required, be first caused to flow through a low temperature condenser solvent removal system, and then be caused to flow through an enclosed filter solvent removal system. Said low temperature condenser system, it will be appreciated will remove approximately ninty-nine (99%) percent of water vapor present, and pass the resulting mixture of water vapor and nebulized sample particles on to said enclosed filter solvent removal system. Said enclosed filter solvent removal system will then consistantly provide nebulized sample particles from which has been removed in excess of ninety-nine-and-nine-tenths (99.9%) percent of solvent vapor originally present therewith. When an organic based solvent is present the low temperature condenser solvent removal system will not be as effective in its removal, (e.g. it will remove approximately fifty (50%) percent thereof), but said enclosed filter solvent removal system is capable of performing removal of the remaining organic solvent vapor. This is because even relatively large flow rates of organic solvent vapor into an enclosed filter solvent removal system have not been observed to cause instability in the solvent vapor removing capacity thereof.

The present invention is then found is the use of a sequential combination of low temperature condenser and enclosed filter solvent removal systems. It is to be noted that typically, although not necessarily, a low temperature condenser solvent removal system will be the first in said sequence, followed by an enclosed filter solvent removal system. It is also to be understood that a desolvation system will precede said first low temperature condenser solvent removal system, and additional desolvation systems can be present between said first low temperature condenser solvent removal system and a following enclosed filter solvent removal system. As well, multiple stages of sequentially oriented low temperature condenser and enclosed filter, (with or without intervening desolvation systems), can be present. As well, the present invention includes systems in which multiple solvent removal systems of one type, (ie low temperature condenser and enclosed filter), are present without an intervening solvent removal system or the other type being present therebetween.

It is therefor a purpose of the present invention to teach a system and method of its use for removing solvent vapor from a mixture of solvent vapor and nebulized sample particles which is equally successful at removing solvent vapor whether said solvent vapor is aqueous or organic, and regardless of the flow rate of said solvent vapor into said system.

It is another purpose of the present invention to teach that low temperature condenser and enclosed filter solvent removal systems should be utilized in sequential combination, with or without intervening desolvation systems, to provide a solvent removal system which meets the first purpose stated above.

It is yet another purpose of the present invention to teach that a sequential combination of low temperature condenser and enclosed filter solvent removal systems can be comprised of a multiplicity of each of said low temperature condenser and enclosed filter solvent removal systems, with or without intervening desolvation systems present after the first solvant removal system in said sequential combination system.

It is still yet another purpose of the present invention to teach that the order of low temperature condenser and enclosed filter solvent removal systems in a sequential combination thereof is preferably, but not necessarily, initiated by a low temperature condenser following a desolvation system, and that said sequence typically, but not necessarily, alternates low temperature condenser and enclosed filter solvent removal systems, with or without intervening desolvation systems.

DETAILED DESCRIPTION

Figure 1:
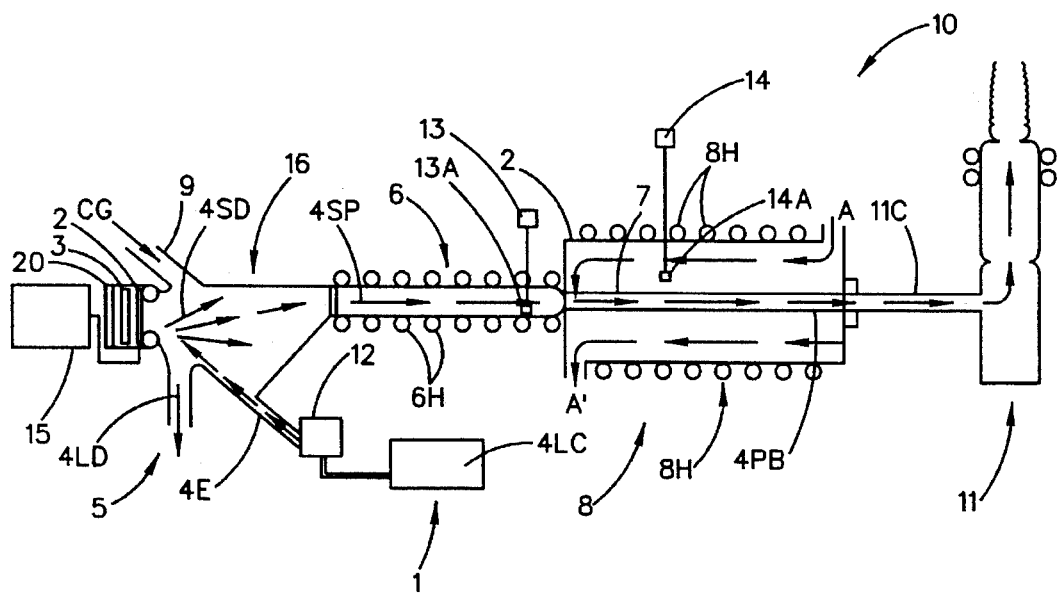
FIG. 1 shows a system utilizing an ultrasonic nebulizer and a single enclosed filter solvent removal system, which enclosed filter is present inside a containing structure which allows effecting a solvent vapor removing flow of gas at the outside surface of said enclosed filter.
Figure 3:
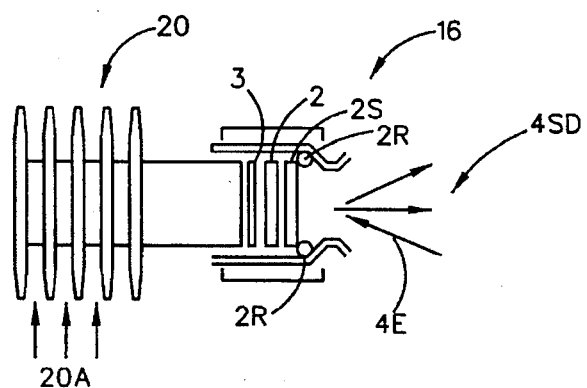
FIG. 3 shows an expanded view of the preferred arrangement of vibrational energy producing associated elements in the ultrasonic nebulizer demonstrated in FIG. 1. A polyimide film or equivalent, piezoelectric crystal or equivalent, insulator and "O" ring are shown in exploded form for easier observation.

Turning now to the Drawings, there is shown in FIG., 1 a diagramatic view, of one embodiment of the overall system of an ultrasonic nebulizer and a single enclosed filter solvent removal sample introduction invention (10). In the following discussion the CETAC TECHNOLOGIES INC. U5000AT ultrasonic nebulizer is used as an example of a sample solution nebulizer to aid with understanding of a typical system, but it is to be understood that the present invention can be utilized with any type of sample solution nebulizer. (See the Background Section of this Disclosure for a discussion of numerous types of sample solution nebulizers). Continuing, FIG. 1 shows a source (1) of sample solution (4LC) attached to means (12) for causing said sample solution (4LC) to impinge upon piezoelectric crystal or equivalent (2) in aerosol chamber system (16). (The sample solution (4LC) can originate from any source of liquid sample). The aerosol chamber (16) provides essentially tubular means for entering a sample solution flow thereto and an impinging sample solution flow is identified by numeral (4E), the flow rate of which is typically, but not necessarily one (1) millliter per minute. Piezoelectric crystal or equivalent (2) is caused to vibrate, typically but not necessarily at one-and-three-tenths (1.3) Megahertz, by inclusion in an electric power source and oscillator circuit (15). Also shown is a polyimide film or equivalent (3) which serves to reflect and help focus vibrational energy developed by piezoelectric crystal or equivalent (2) to the location thereon, or in close proximity thereto at which the sample solution (4E) impinges, in front of said piezoelectric crystal or equivalent (2). Said polyimide film or equivalent (3), also serves as a compressible buffer means by which the piezoelectric crystal or equivalent (2) is attached to the aerosol chamber system (16) structural heat sink (20). The aerosol chamber provides an essentially tubular structural heat sink connection means with a constriction present therein. FIG. 3 shows an expanded view of the structural heat sink (20) at its point of connection to the aerosol chamber (16). FIG. 3 also shows in exploded fashion the polyimide film or equivalent (3), the piezoelectric crystal or equivalent (2) and an insulator (2S) which is typically, but not necessarily, made of a glass material, present on the front surface of the piezoelectric crystal or equivalent (2). The purpose of the insulator (2S) is to protect the piezoelectric crystal or equivalent against corrosion etc. due to components in sample solutions impinged thereon. Also note by reference to FIG. 3 that when the structural heat sink (20) is slid fully into the aerosol chamber (16), the polyimide film or equivalent (3), piezoelectric crystal or equivalent (2) and insulator (2S) will be sandwiched together between the structural heat sink and the constriction in the structural heat sink connection means in the aerosol chamber. Also note that "O" ring (2R) will then serve to prevent crevasses from existing at the point of connection between the aerosol chamber (16) and the vibrational energy producing elements of the invention. Crevasses, as mentioned in the Background Section of this Disclosure, in other ultrasonic nebulizing systems have led to sample carry-over problems. It is mentioned that electrical contact to the piezoelectric crystal or equivalent (2) from the electric oscillator circuitry (15) can be by any convenient connector pathway, and is typically by way of an opening in the structural heat sink (20). Also note in FIG. 3 the indication of cool air flow (20A) over fins in the structural heat sink (20). Said fins are located distally to the point of the structural heat sink which contacts the polyimide film or equivalent. The present invention uses air cooling and thereby avoids the complications associated with liquid cooling systems discussed in the Background Section of this Disclosure. Continuing, the compressible nature of the polyimide film or equivalent (3) material prevents the piezoelectric crystal or equivalent (2) from repeatedly vibrating against the rigid aerosol chamber system (16) or structural heat sink (20) to which it is interfaced during operation. Said buffering prevents damage to the piezoelectric crystal or equivalent (2). Also, when the polyimide film or equivalent (3) is in place it acts as a uniform contacting heat conducting interface between the vibrating piezoelectric crystal or equivalent (2) and the aerosol chamber system (16) or structural heat sink (20). Uniform heat removal, and piezoelectric crystal or equivalent (2) to aerosol chamber (16) and structural heat sink (20) vibrational contact buffering during use, serve to stabilize the operation of and prolong the lifetime of the piezoelectric crystal or equivalent (2) of the present invention. Typically a lifetime of years, rather than weeks (as is typically the case with piezoelectric crystals or equivalent in other ultrasonic nebulizer systems), is achieved. As mentioned above that the piezoelectric crystal or equivalent (2) of the present invention is, in the preferred embodiment, cooled by flowing air past structural heat sink (20). That is, no liquid coolant is required. As a result, corrosion problems associated with liquid cooled ultrasonic nebulizers as disclosed in the Background Section of this Disclosure are eliminated.

Continuing, interaction between vibrational energy produced by said piezoelectric crystal or equivalent (2) and impinging sample solution (4E) causes production of nebulized sample solution droplets (4SD). Seventy (70%) percent of said nebulized sample solution droplets are typically of a diameter of less than thirteen (13) microns when the frequency of vibration of the piezoelectric crystal or equivalent in the present invention is one-and-three-tenths (1.3) Megahertz. Larger diameter droplets (4LD) typically fall under the influence of gravity, and are removed from the system (10) at drain (5) of aerosol chamber system (16). The remaining smaller diameter nebulized sample solution droplets (4SD) are caused to flow, typically under the influence of a pressure gradient created by entering a typically tangentially directed carrier gas flow "CG" at essentially tubular carrier gas inlet port (9), into desolvation chamber (6) in which the temperature is caused to exceed the boiling point of the solvent which is present, by heater means (6h). The carrier gas "CG" flow rate is typically one-half (0.5) liters per minute. In said desolvation chamber (6) the nebulized sample solution droplets are desolvated to form a mixture of solvent vapor and nebulized sample particles (4SP). It is mentioned that a tangentially oriented carrier gas flow which follows a spiral-like path locus which is essentially perpendicular to the surface of the piezoelectric crystal or equivalent (2) and toward desolvation chamber (6), helps to prevent sample "carry-over" and "pulsation" problems, as discussed in prior sections of this Disclosure. It is again mentioned that no crevasses are present in the aerosol chamber which can retain sample. Continuing, the mixture of solvent vapor and nebulized sample particles (4SP) is caused to flow, typically under the influence of the pressure gradient created by entering carrier gas flow "CG", into an enclosed filter (7) of solvent removal system (8). Heater means (8h) serve to keep the temperature in the solvent removal system (8) above the boiling point of the solvent present. Typical temperatures maintained within the solvent removal means are in the rage of forty (40) and one-hundred-and-fifty (150) degrees centigrade, depending on the solvent being used.

Enclosed filter (7) is made of a material which allows solvent vapor to diffuse therethrough, but which retains the nebulized sample particles therein. A solvent vapor removing gas flow "A" is caused to enter solvent removal system (8) at inlet port (8a), flow around the outside of enclosed filter (7), and exit at outlet port (8b). Said solvent vapor removing gas flow is indicated as "A" at the inlet port (8a) and as "A'" at the outlet port (8b). Said solvent vapor removal gas flow serves to remove solvent vapor which diffuses through said enclosed filter (7). The nebulized sample particles (4SP) which remain inside of enclosed filter (7) are then caused to flow, typically under the influence of the above identified pressure gradient, into an Inductively Coupled Plasma analysis system, or other analysis system (11) by way of connection means (11C). Said flow is identified by the numeral (4PB).

It is mentioned that enclosed filter (7) is typically made of PTFE material and is available under the tradename of GORE-TEX. Said material has a pore size of one (1) to two (2) microns and a porosity of seventy (70%) percent. Tubular forms of the filter are available with one (1), two (2) and four (4) milimeter inner diameters and are identified as GORE-TEX micro porous tubings. Said microporous tubular filters are especially suitable for use in the present invention. The GORE-TEX PTFE material has been found to provide the present invention with improved operating characteristics by allowing a relatively short length, (e.g. less than forty (40) centimeters), of enclosed filter to be used, while still allowing efficient removal of solvent vapor. Enclosed filters made of other commercially available materials must typically be five (5) or more fold longer to provide equivalent solvent removal capability. A shorter length of enclosed filter means that the enclosed filter contains a smaller volume and, hence, that sample "carry-over" from one analysis procedure to a subsequent analysis procedure is greatly reduced. In addition, said enclosed filter, being of essentially linear geometry or at worst requiring only gradual curves therein to fit into reasonably sized system containments, does not present a sample transported therethrough with turbulence creating severe direction reversals. Longer enclosed filters made from inferior pore size and porosity parameter filter materials typically do include such turbulence creating sample flow path direction reversals. The result is increased sample "carry-over" based problems during use.

Also shown in FIG. 1 are desolvation chamber and solvent removal system thermocouples (13A) and (14A) respectively, and associated heating controllers (13) and (14) respectively. Said elements monitor and control of the temperatures in the associated invention system components.

Figure 2:
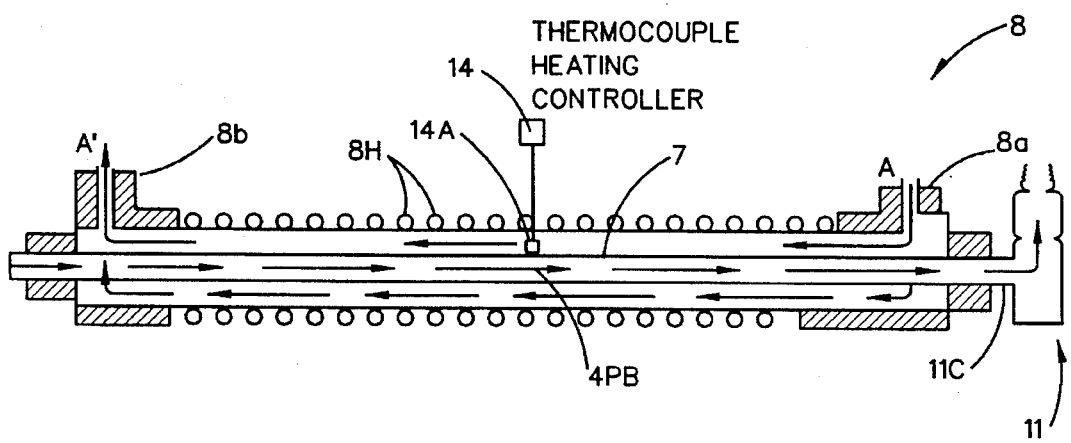
FIG. 2 shows an expanded view of an enclosed filter solvent removal system as demonstrated in FIG. 1.

Turning now to FIG. 2, there is shown an expanded diagramatic view of a solvent removal system (8). Note in particular the inlet port (8a) at which solvent removal gas flow "A" is entered, and outlet port (8b) at which solvent vapor gas flow "A'" exits. While the solvent removal system (8) can be of any functional geometry, the preferred embodiment is a tube of approximately one-half (0.5) inch in diameter, or less. Said shape and size provides an effective volume flow rate therethrough when a typical one (1) liter per minute solvent vapor removal gas flow "A"–"A'" is entered thereto. It is preferred to cause solvent vapor removal gas flow "A"–"A'" to flow in the direction as shown because the relative solvent saturation of the gas in solvent vapor removal gas flow "A"–"A'" along its locus of flow, is closely matched to that of the solvent vapor inside the enclosed filter (7). However, solvent vapor removal gas flow could be caused to flow in a direction opposite, (e.g. "A'"–"A"), to that shown and be within the scope of the present invention. Also shown in FIG. 2 are heater element (8h), nebulized sample particles flow (4PB) and connection means (12) to partially shown inductively coupled plasma or other sample analysis system (11). It is also mentioned that it is within the scope of the present invention to utilize a chemical dessicant or a dry gas in solvent vapor removal gas flow "A"–"A'" or "A'"–"A".

It is also mentioned that while distinct elements are shown and described for performing various described functions in the present invention, it is within the scope of the present invention to perform more than one function in one element of the overall system of the present invention, or to combine various elements of the overall system into composite elements. For instance, desolvation chamber (6) and solvent removal system (8) might be combined into one system.

It will be appreciated, in view of the above, that the present invention provides a small internal volume enclosed filter (7) in which solvent vapor is filtered away from nebulized sample particles (4PB), the volume inside a one (1) to four (4) millmeter inner diameter GORE-TEX tube essentially comprising said enclosed filter volume. As a result, sample carry-over problems are minimized. In addition, it is to be noted the presently discussed embodiment of the present invention system (10) does not utilize low temperatures to condense solvent vapor. Also, the present invention can be operated to provide high solvent removal efficiency by control of desolvation chamber (6) and solvent removal system (8) temperatures in conjunction with other system parameters, regardless of solvent type, (e.g. water, organic etc.). This is considered a very important point. The first embodiment of the present invention, thus, provides a sensitive, sample conserving, highly efficient system for providing highly nebulized sample particles and transporting them to a plasma or other analysis system.

Also shown in FIG. 2 are thermocouple (14A) and heating control (14).

It is also to be understood that while the desolvation chamber (6) and solvent removal system (8) are each shown as being single units in the drawings, it is possible for each to be comprised of multiple sequential units.

Continuing, as described in the Disclosure of the Invention Section of this Disclosure, it has been determined empirically that a sample introduction system as just described presents with a problem when used exclusively to remove aqueous solvent vapor. While sample solution nebulization and resulting nebulized sample solution droplets desolvation are achieved with great success, solvent removal by the enclosed filter solvent removal system provides eradict, often cyclical, operational efficiency when the solvent vapor rate of entry exceeds some critical value specific to an enclosed filter of specific design parameters. This problem, however, has not been found to occur when organic solvent vapor is present, or when the flow rate of aqueous solvent vapor is maintained below said critical value. It is this problem the present invention solves. In said scenarios the solvent removal efficiency is typically ninty-nine-and-nine-tenths (99.9%) percent or better.

Figure 4:
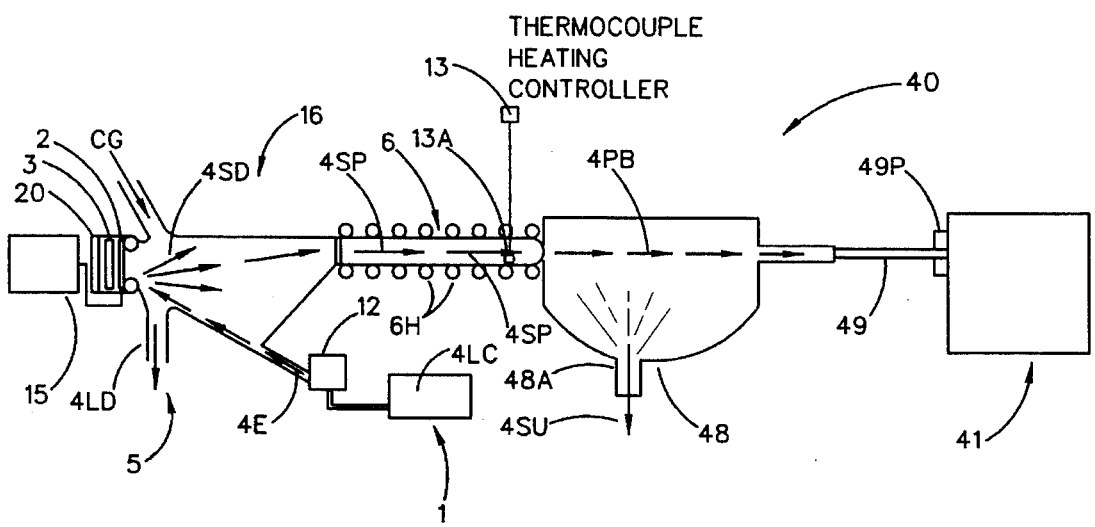
FIG. 4 shows modified system utilizing an ultrasonic nebulizer and a single enclosed filter solvent removal system, which enclosed filter is present inside a low temperature condenser system.

Turning now to FIG. 4, there is shown a diagramatic view of a the exemplary ultrasonic nebulizer utilizing a low temperature condenser solvent removal sample introduction invention (40). The discussion relating to FIGS. 1 and 3 is equally valid to point at which the mixture of solvent vapor and desolvated sample particles (4PB) enters the low temperature condenser solvent removal system (40). Solvent vapor exiting desolvation systems (6) is transported into the low temperature condenser (48), in which it condenses and flows out of drain (48A), said flow being indicated by (4SU). Entering nebulized desolvated sample particles (4PB) are transported toward an analysis system (41), under the influence of an entered carrier gas flow "CG", by way of connection means (49) from the low temperature condenser (48) and connection means (49P) at the analysis system (41).

Figure 5:
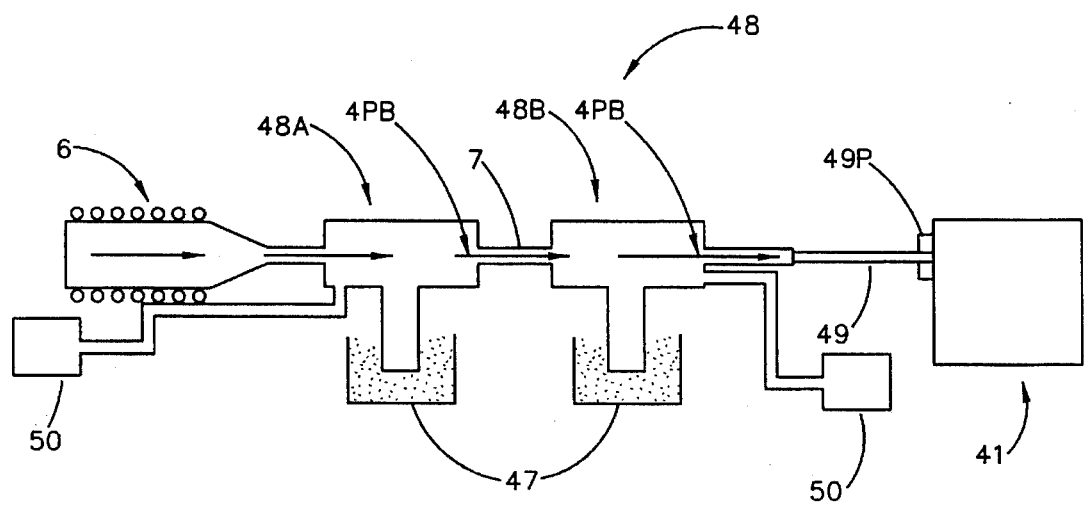
FIG. 5 shows an expanded view of an enclosed filter solvent removal system as demonstrated in FIG. 4.

Turning now to FIG. 5, there is shown an expanded exemplary diagramatic view of the low temperature condenser (48) in FIG. 4. Note that two sections (48A) and (48B) are shown. Note that it is within the scope of the present invention to provide a solvent removal system with more or less than two low temperature condenser (48) sections, just as other elements of the present invention can be of other than exactly shown, but functional, construction. Also shown in FIG. 5 are optional vacuum pumps (50) and low temperature maintaining liquid, typically liquid nitrogen or a mixture of dry ice and isopropanol (47). It is noted that use of ethylene glycol, peltier and closed cycle techniques can also serve to effect a suitable low temperature in a low temperature condenser solvent removal system.

The sample introduction system of FIG. 4 has been found to be very effective (e.g. ninety-nine (99%) percent) in removing water vapor introduced thereto, but not as effective in removing organic solvent vapor introduced thereto, (e.g. fifty (50%) percent effective).

In light of the above, it must be understood that when aqueous solvent vapor is present, and is caused to flow exclusively into an enclosed filter solvent removal system at relatively great flow rates, the exiting mixture of nebulized sample particles and water vapor can be erratic as regards the level of water vapor present. This can lead to instability in, for instance, plasmas into which said mixture of nebulized sample particles and water vapor is injected. The present invention teaches that the identified problem can be overcome by providing a sequential combination of low temperature condenser and enclosed filter solvent removal systems into which the output of a desolvation system, (identified by numeral (6) the FIGS. 1 and 4), feeds.

Figure 6:
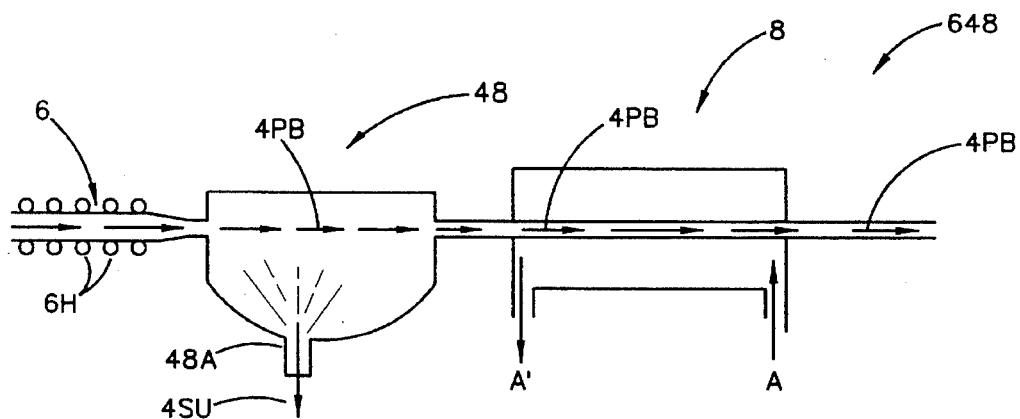
FIG. 6 shows a sequential combination solvent removal systems comprising one low temperature condenser and one enclosed filter solvent removal system which are functionally interconnected to one another.

FIG. 6 shows the outlet of a low temperature condenser (48) solvent removal system as shown in FIGS. 4 and 5 functionally interconnected with the inlet of an enclosed filter (8) solvent removal system, to form the preferred embodiment of the present invention. In use an entering mixture of solvent vapor and nebulized sample particles will be provided at the outlet of the enclosed filter (8) solvent removal system with an exceptionally stable and low level of solvent vapor present regardless if said solvent is aqueous or organic. The low temperature condenser (48) solvent removal system serving to remove approximately ninety-nine (99%) percent of aqueous solvent present and the enclosed filter (8) solvent removal system serving to remove upwards of ninety-nine-and-nine-tenths (99.9%) percent or better of entering solvent vapor whether said solvent is aqueous or organic. The use of a first stage low temperature condenser (48) solvent removal system prevents overwhelming said enclosed filter (8) solvent removal system with water vapor to the point that it operates with eradict or cyclical efficiency. It is the surprisingly good results provided by the sequential combination (648) solvent system which forms the basis of the present invention. As described in the Disclosure of the Invention Section, the relative standard deviation in data achieved from an inductively coupled plasma sample analysis system was improved by a factor of five (5) when the present invention was used in place of an exclusive enclosed filter solvent removal system, when a one (1) part per million manganese sample in an aqueous solution provided by the present invention, was analyzed thereby.

Figure 7A:
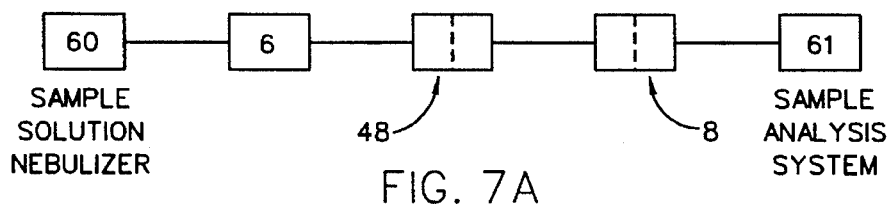
FIGS. 7a and 7b show two sequential combination low temperature condenser and enclosed filter solvent removal system configurations in combination with nebulizer, desolvation and sample analysis systems.
Figure 7B:
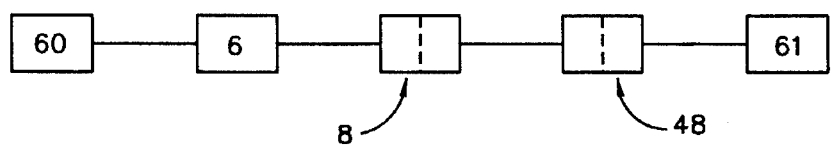
Figure 7C:
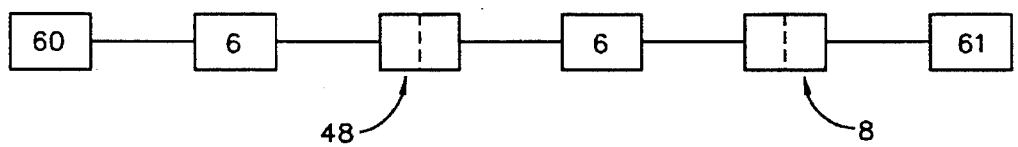
FIGS. 7c and 7d show two sequential combination low temperature condenser and enclosed filter solvent removal system configurations with a second desolvation system intervening therebetween, in combination with nebulizer desolvation and sample analysis systems.
Figure 7D:
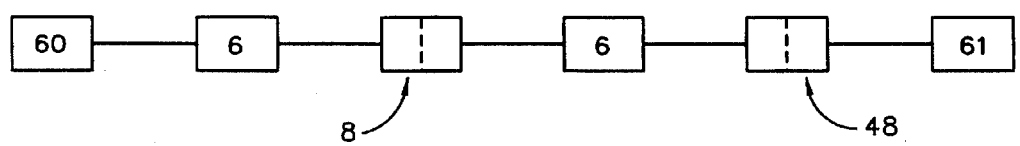

Turning now to FIGS. 7a, 7b, 7c and 7d, there are shown various configurations of the present invention in block diagram form. That is, a sample solution nebulizer, (of any type, not necessarily an ultrasonic nebulizer), system is identified by numeral (60), desolvation chamber(s) is/are identified by numeral(s) (6), enclosed filter solvent removal system(s) is/are identified by numeral(s) (8), a sample analysis system is identified by numeral (61) and in addition low temperature condenser solvent removal system(s) is/are identified by numeral(s) (48). The present invention provides that both enclosed filter solvent removal system(s) (8) and low temperature condenser solvent removal system(s) (48) be used in sequential combination, with desolvation system(s) (6) present prior to the first solvent removal system, and optionally present between sequentially attached solvent removal systems. It is noted that typically the first solvent removal system will be a low temperature condenser solvent removal system (48) as shown by FIGS. 7a and 7c so that, as described in the Disclosure of the Invention Section of this Disclosure, approximately ninty-nine (99%) percent of entering aqueous solvent vapor is removed thereby prior to entering an enclosed filter solvent removal system (8). This prevents enclosed filter solvent removal systems (8) from performing eradictly or with cyclical efficiency when aqueous solvent is present, again as described in the Disclosure of the Invention Section. The present invention provides for any number of sequentially oriented solvent removal systems. That includes the case where two solvent removal systems of one type, (ie. two low temperature condenser (48) or two enclosed filter (8) solvent removal systems), are sequentially attached to one another, (note that the dotted lines in FIGS. 7a–7d can be interpreted to show that a block is optionally considered to be comprised of multiple similar solvent removal systems rather than to represent a single such system), and where low temperature condenser (48) and enclosed filter (8) solvent removal systems alternate, with or without intervening desolvation systems (6) therebetween, as long as at least one solvent removal system of each type, (ie. low temperature condenser (48) and enclosed filter (8)), are present. The Claims are to be interpreted to include any such configuration.

In summary then, the present invention is a sequential combination solvent removal system comprised of a at least one low temperature condenser (48) and at least one enclosed filter (8) solvent removal systems, which sequential combination of low temperature condenser (48) and enclosed filter (8) solvent removal systems allow production of an exiting mixture of nebulized, desolvated, sample particles and solvent vapor, in which the level of solvent vapor present is essentially constant whether the solvent is aqueous or organic, and regardless of the type of nebulizer which nebulizes a sample solution and of the flow rate of said solvent vapor which enters said sequential combination solvent removal system.

It is to be understood that while inductively coupled plasma based systems were used as examples of sample analysis systems herein, any sample analysis system, (e.g. microwave induced plasma, corona discharge, flame, atomic emission and atomic absorbtion systems, D.C. plasma discharge systems and mass spectrometers etc.), is to be considered equivalent for the purpose of applicability to the present invention.

It is also to be understood that sample solutions can originate from any source and can be subjected to component separation steps prior to being entered into a system for introducing samples as sample flows. This might be the case, for instance, where the sample solution is derived from a liquid chromatography source.

Having hereby disclosed the subject matter of this invention, it should be obvious that many modifications, substitutions, and variations of the present invention are possible in light of the teachings. It is therefore to be understood that the invention may be practiced other than as specifically described, and should be limited in breadth and scope only by the Claims.

I claim:

1. A sequential combination solvent removal system comprising a low temperature condenser solvent removal system and an enclosed filter solvent removal system functionally interconnected to one another; for use in providing desolvated nebulized sample particles to a sample analysis system with any solvent vapor present being at a low essentially constant level, regardless of type of sample solution nebulizer used to produce nebulized sample solution droplets, which when desolvated by a desolvation system provide said nebulized sample particles in mixture with solvent vapor, whether said solvent is aqueous or organic and regardless of the flow rate of said solvent vapor into said sequential combination solvent removal system; which low temperature condenser solvent removal system comprises an enclosed volume with a drain present at a lower extent thereof and means for maintaining a low temperature therein, such that solvent vapor entered thereinto during use condenses and exits via said drain while desolvated nebulized sample particles entered thereinto during use flow therethrough; and which enclosed filter solvent removal system comprises an essentially tubular shaped enclosed filter made of a material which allows solvent vapor entered thereinto during use to diffuse therethrough, but which retains desolvated nebulized sample particles entered thereinto during use therein, and which enclosed filter solvent removal system further comprises means for causing a solvent vapor removing gas flow around the outside of said enclosed filter, such that solvent vapor entered to said enclosed filter during usc which diffuses through said enclosed filter and is removed by said solvent vapor removing gas flow, while desolvated nebulized sample particles entered into said enclosed filter remain therein and flow therethrough during use; such that desolvated nebulized sample particles entered into said sequential combination solvent removal system during use travel therethrough and exit into a sample analysis system.

2. A sequential combination solvent removal system as in claim 1, in which the low temperature condenser solvent removal system is functionally interconnected, at an inlet end thereof, to an outlet end of said desolvation system, which desolvation system serves to heat nebulized sample solution droplets entered thereinto from a sample solution nebulizer system, to produce said mixture of desolvated nebulized sample particles and solvent vapor, and in which said enclosed filter solvent removal system is functionally interconnected, at an inlet end thereof to an outlet end of said low temperature condenser solvent removal system.

3. A sequential combination solvent removal system as in claim 1, in which the low temperature condenser solvent removal system is functionally interconnected, at an inlet end thereof, to an outlet end of said desolvation system, which desolvation system serves to heat nebulized sample solution droplets entered thereinto from a sample solution nebulizer system, to produce said mixture of desolvated nebulized sample particles and solvent vapor, and in which said enclosed filter solvent removal system is functionally interconnected, at an inlet end thereof to an outlet end of a second desolvation system, the inlet end thereof being functionally interconnected to an outlet end of said low temperature condenser solvent removal system.

4. A sequential combination solvent removal system as in claim 1, in which the enclosed filter solvent removal system is functionally interconnected, at an inlet end thereof, to an outlet end of said desolvation system, which desolvation systems serves to heat nebulized sample solution droplets entered thereinto from a sample solution nebulizer system, to produce said mixture of desolvated nebulized sample particles and solvent vapor, and in which said low temperature condenser solvent removal system is functionally interconnected, at an inlet end thereof to an outlet end of said enclosed filter solvent removal system.

5. A sequential combination solvent removal system as in claim 1, in which the enclosed filter solvent removal system is functionally interconnected, at an inlet end thereof, to an outlet end of said desolvation system, which desolvation system serves to heat nebulized sample solution droplets entered thereinto from a sample solution nebulizer system, to produce said mixture of desolvated nebulized sample particles and solvent vapor, and in which said low temperature condenser solvent removal system is functionally interconnected, at an inlet end thereof to an outlet end of a second desolvation system, the inlet end thereof being functionally interconnected to an outlet end of said enclosed filter solvent removal system.

6. A sequential combination solvent removal system as in claim 1 in which the sample solution nebulizer is pneumatic.

7. A sequential combination solvent removal system as in claim 1 in which the sample solution nebulizer is a direct injection total consumption micro nebulizer.

8. A sequential combination solvent removal system as in claim 1 in which the sample solution nebulizer is ultrasonic.

9. A sequential combination solvent removal system as in claim 1 in which the sample solution nebulizer is a thermalspray type.

10. A sequential combination solvent removal system as in claim 1 in which the sample solution nebulizer is a combination thermal spray and pneumatic type.

11. A sequential combination solvent removal system as in claim 1 in which the sample solution nebulizer is a glass frit.

12. A sequential combination solvent removal system as in claim 1 in which the sample solution nebulizer is a combination ultrasonic and pneumatic type.

13. A sequential combination solvent removal system as in claim 1 in which the sample solution nebulizer is a jet impact type.

14. A method of providing a mixture of nebulized sample particles and a low, essentially constant level of solvent vapor, for introduction into a sample analysis system, comprising the steps of:

a. obtaining a sequential combination solvent removal system comprising a low temperature condenser solvent removal system and an enclosed filter solvent removal system functionally interconnected to one another; for use in providing desolvated nebulized sample particles to a sample analysis system with any solvent vapor present being at a low essentially constant level, regardless of type of sample solution nebulizer used to produce nebulized sample solution droplets, which when desolvated by a desolvation system provide said nebulized sample particles in mixture with solvent vapor, whether said solvent is aqueous or organic and regardless of the flow rate of said solvent vapor into said sequential combination solvent removal system; which low temperature condenser solvent removal system comprises an enclosed volume with a drain present at a lower extent thereof and means for maintaining a low temperature therein, such that solvent vapor entered thereinto during use condenses and exists via said drain while desolvated nebulized sample particles entered thereinto during use flow therethrough; and which enclosed filter solvent removal system comprises an essentially tubular shaped enclosed filter made of a material which allows solvent vapor entered thereinto during use to diffuse therethrough, but which retains desolvated nebulized sample particles entered thereinto during use therein, and which enclosed filter solvent removal system further comprises means for causing a solvent vapor removing gas flow around the outside of said enclosed filter, such that solvent vapor entered into said enclosed filter during use which diffuses through said enclosed filter and is removed by said solvent vapor removing gas flow, while desolvated nebulized sample particles entered into said enclosed filter are caused to remain therein and flow therethrough; such that desolvated nebulized sample particles entered into said sequential combination solvent removal system during use travel therethrough and exit into a sample analysis system;

b. entering a sample solution to said nebulizer such that it produces nebulized sample solution droplets;

c. causing said nebulized sample solution droplets to flow through said desolvation system, in which desolvation system heat is applied such that solvent present is vaporized resulting in the formation of said mixture of nebulized sample particles and said solvent vapor;

d. causing said mixture of nebulized sample particles and solvent vapor to flow into said sequential combination solvent removal system such that essentially all solvent vapor is removed thereby; and e. causing said nebulized sample particles and a low, essentially constant level of solvent vapor to flow from said sequential combination solvent removal system and into said sample analysis system.

15. A method of providing a mixture of nebulized sample particles and a low, essentially constant level of solvent vapor, for introduction into a sample analysis system as in claim 14, in which the mixture of nebulized sample particles and solvent vapor flow first enters and flows through said low temperature condenser solvent removal system and then said enclosed filter solvent removal system.

16. A method of providing a mixture of nebulized sample particles and a low, essentially constant level of solvent vapor, for introduction into a sample analysis system as in claim 14, in which the mixture of nebulized sample particles and solvent vapor flow first enters and flows through said enclosed filter solvent removal system and then said low temperature condenser solvent removal system.

17. A method of providing a mixture of nebulized sample particles and a low, essentially constant level of solvent vapor, for introduction into a sample analysis system as in claim 15 which further comprises the step of causing said mixture of nebulized sample particles and solvent vapor exiting said low temperature condenser solvent removal system to pass through a second desolvation system prior to entering said enclosed filter solvent removal system, the purpose thereof being to assure all solvent remaining present is vaporized.

18. A method of providing a mixture of nebulized sample particles and a low, essentially constant level of solvent vapor, for introduction into a sample analysis system as in claim 16, which further comprises the step of causing said mixture of nebulized sample particles and solvent vapor exiting said enclosed filter solvent removal system to pass through a second desolvation system prior to entering said low temperature condenser solvent removal system, the purpose thereof being to assure all solvent remaining present is vaporized.

19. A method of providing a mixture of nebulized sample particles and a low, essentially constant level of solvent vapor, for introduction into a sample analysis system as in claim 14, in which the mixture of nebulized sample particles and solvent vapor is caused to flow through more than one low temperature condensor solvent removal system.

20. A method of providing a mixture of nebulized sample particles and a low, essentially constant level of solvent vapor, for introduction into a sample analysis system as in claim 14, in which the mixture of nebulized sample particles and solvent vapor is caused to flow through more than one enclosed filter solvent removal system.

* * * * *